(12) United States Patent
Fuji et al.

(10) Patent No.: US 8,603,172 B2
(45) Date of Patent: Dec. 10, 2013

(54) CAGE

(75) Inventors: Takeshi Fuji, Hyougo (JP); Kazuya Oribe, Aichi (JP)

(73) Assignee: Showa Ika Kohgyo Co., Ltd., Aichi (JP)

(*) Notice: Subject to any disclaimer, the term of this patent is extended or adjusted under 35 U.S.C. 154(b) by 319 days.

(21) Appl. No.: 12/366,096

(22) Filed: Feb. 5, 2009

(65) Prior Publication Data
US 2009/0204214 A1    Aug. 13, 2009

(30) Foreign Application Priority Data

Feb. 7, 2008 (JP) ................................. 2008-028127
Jan. 13, 2009 (JP) ................................. 2009-004482

(51) Int. Cl.
*A61F 2/44* (2006.01)

(52) U.S. Cl.
USPC ..................................... 623/17.16; 623/17.11

(58) Field of Classification Search
USPC ........................................... 623/17.11, 17.16
See application file for complete search history.

(56) References Cited

U.S. PATENT DOCUMENTS

| | | | |
|---|---|---|---|
| 4,834,757 A * | 5/1989 | Brantigan | 623/17.11 |
| 5,609,636 A * | 3/1997 | Kohrs et al. | 623/17.16 |
| 5,645,084 A | 7/1997 | McKay | |
| 5,669,909 A | 9/1997 | Zdeblick et al. | |
| 5,782,919 A | 7/1998 | Zdeblick et al. | |
| 5,888,222 A | 3/1999 | Coates et al. | |
| 5,984,967 A | 11/1999 | Zdeblick et al. | |
| 6,206,922 B1 | 3/2001 | Zdeblick et al. | |
| 6,245,072 B1 | 6/2001 | Zdeblick et al. | |
| 6,346,122 B1 * | 2/2002 | Picha et al. | 623/17.11 |
| 6,375,655 B1 | 4/2002 | Zdeblick et al. | |
| 6,471,724 B2 | 10/2002 | Zdeblick et al. | |
| 6,595,995 B2 | 7/2003 | Zdeblick et al. | |
| 6,613,091 B1 | 9/2003 | Zdeblick et al. | |
| 6,645,206 B1 | 11/2003 | Zdeblick et al. | |
| 6,695,851 B2 | 2/2004 | Zdeblick et al. | |
| 7,238,186 B2 | 7/2007 | Zdeblick et al. | |

(Continued)

FOREIGN PATENT DOCUMENTS

| | | |
|---|---|---|
| EP | 1082950 | 3/2001 |
| JP | 8-266565 A | 10/1996 |

OTHER PUBLICATIONS

Office Action from E.P.O., mail date is Dec. 29, 2010.
English language Abstract of JP 8-266565 A, Oct. 15, 1996.

(Continued)

*Primary Examiner* — Michael T Schaper
(74) *Attorney, Agent, or Firm* — Greenblum & Bernstein, P.L.C.

(57) ABSTRACT

A cage interposed between a pair of vertebral bodies, wherein both left and right side surfaces of a cage body are formed in a smooth surface, both upper and lower surfaces of the cage body are provided with a large number of projections arranged in a longitudinal direction and a lateral direction, tip end surfaces of the large number of projections substantially match with a virtual arc curved surface formed around an axis in the longitudinal direction, and angles of inner end edges of the projections close to left and right side surfaces are more acute. A longitudinal through hole is formed in the cage body in its longitudinal direction so as to penetrate the cage body, and both left and right side surfaces and both upper and lower surfaces of the cage body are provided with communication holes which are in communication with the longitudinal through hole. The communication holes are circular holes having a common diameter.

6 Claims, 8 Drawing Sheets

(56) References Cited

U.S. PATENT DOCUMENTS

| | | |
|---|---|---|
| 7,300,440 B2 | 11/2007 | Zdeblick et al. |
| 7,534,266 B2 * | 5/2009 | Kluger ....................... 623/17.11 |
| 2001/0031968 A1 * | 10/2001 | Dorchak et al. ................ 606/90 |
| 2002/0116065 A1 * | 8/2002 | Jackson ..................... 623/17.16 |
| 2004/0122518 A1 | 6/2004 | Rhoda |
| 2004/0153089 A1 | 8/2004 | Zdeblick et al. |
| 2005/0192669 A1 * | 9/2005 | Zdeblick et al. ........... 623/17.11 |
| 2007/0270956 A1 | 11/2007 | Heinz |
| 2008/0065219 A1 * | 3/2008 | Dye ........................... 623/17.16 |
| 2008/0195209 A1 * | 8/2008 | Garcia et al. ................ 623/17.16 |
| 2009/0043394 A1 | 2/2009 | Zdeblick et al. |

OTHER PUBLICATIONS

English language Abstract of EP 1082950, Mar. 14, 2001.

* cited by examiner

＃ CAGE

BACKGROUND OF THE INVENTION

1. Field of the Invention

The present invention relates to a cage to be interposed between a pair of vertebral bodies in place of a degenerative intervertebral disk after it is removed, and, more particularly to a cage with an excellent home position maintaining ability which can be placed between a pair of vertebral bodies easily, and in which after the cage is placed, its home position is maintained without moving the cage.

2. Description of the Related Art

To place a cage between a pair of vertebral bodies in place of a degenerative intervertebral disk after it is removed has been conventionally carried out, and cages of various shapes have been developed. Japanese Patent Application Laid-open No. H8-266565 describes a cage of a shape closest to that of the present invention.

A cage 81 described in Japanese Patent Application Laid-open No. H8-266565 has a structure as shown in FIG. 1. That is, a cage body 83 of the cage 81 is tapered as an entire configuration, and left and right side surfaces 85 of the cage body 83 are formed in a smooth flat surface. Upper and lower surfaces of the cage body 83 are formed in an arc curved surface. A longitudinal hole 87 is formed in the cage body 83, a cross-sectional shape of the hole 87 is of a vertically long circular shape, and a rear end of the hole 87 is closed with a wall portion 89. The left and right side surfaces 85 of the cage body 83 are respectively provided with communication holes 91A and 91B which are in communication with the hole 87, and long holes 93, which are long in the longitudinal direction, are formed in upper and lower surfaces of the cage body 83.

A thread 95 is formed on an outer peripheral surface of the cage body 83, more precisely, upper and lower surfaces of the cage body 83. Although the thread 95 is cut by the fact that the side surfaces 85 are formed in a flat surface and the upper and lower surfaces of the cage body 83 are formed with the long holes 93, one thread 95A of the rear end makes the round of the cage body 83 without being cut. Tool engaging portions 97 with which a tool used for setting the cage 81 between a pair of vertebral bodies is engaged are formed in front end surface of the cage body 83.

Therefore, in the cage 81, to place the cage 81 between a pair of upper and lower vertebral bodies after a degenerative intervertebral disk is removed, it is necessary to push the cage body 83 in between the pair of vertebral bodies while rotating the cage body 83 so that the thread 95A formed in the rear end of the cage body 83 is first engaged with the upper and lower vertebral bodies. Thus, a placing operation of the cage body is rather troublesome.

Further, there is a problem that the producing cost of the cage becomes high due to the following reasons, i.e., the cage body 83 is tapered, a cross-sectional shape of the hole 87 is long in the vertical direction, shapes and sizes of the communication holes 91A and 91B and the long hole 93 are different from each other.

Further, although the thread 95 is cut, the thread 95 has a long linear shape. Thus, the thread 95 has a problem in engaging ability with the vertebral body, and there is also a problem that the cage 81 is occasionally displaced in position after the cage 81 is placed between a pair of vertebral bodies.

SUMMARY OF THE INVENTION

The present invention has been achieved with such points in mind.

It therefore is an object of the present invention to provide a cage with an excellent home position maintaining ability which can be placed between a pair of vertebral bodies easily, and in which after the cage is placed, its home position is maintained without moving the cage.

To achieve the object, according to a first aspect of the present invention, there is provided a cage which is to be interposed between a pair of vertebral bodies (vertebrae), wherein both left and right side surfaces of a cage body are formed in a smooth surface, both upper and lower surfaces of the cage body are provided with a large number of projections arranged in a longitudinal direction and a lateral direction, tip end surfaces of the large number of projections substantially match with an arc curved surface formed around an axis in the longitudinal direction, and angles of inner end edges of the projections close to left and right side surfaces are more acute.

According to a second aspect of the present invention as it depends from the first aspect, in the cage, a longitudinal through hole is formed in the cage body in its longitudinal direction so as to penetrate the cage body, and both left and right side surfaces and both upper and lower surfaces of the cage body axe provided with communication holes which are in communication with the longitudinal through hole.

According to a third aspect of the present invention as it depends from the first or the second aspect, in the cage, the communication holes are circular holes having a common diameter, and the communication holes formed in both the left and right side surfaces and both the upper and lower surfaces are located on a same plane intersecting with the axis at right angles.

According to a fourth aspect of the present invention as it depends from any one aspect among the first to the third aspects, in the cage, a distance between outer peripheral edges of adjacent communication holes formed in both the left and right side surfaces and both the upper and lower surfaces is smaller than a radius of the communication hole.

According to a fifth aspect of the present invention as it depends from any one aspect among the first to the fourth aspects, in the cage, a tip end of the cage body is tapered with a small diameter. In other words, the cage body is tapered in the longitudinal direction of the cage body in a manner such that a tip end of the cage body has a small diameter.

According to any one aspect among the first to the fifth aspects of the present invention, both of the side surfaces formed in a smooth surface in the cage laterally are toppled to be opposed to the upper and lower vertebral bodies, and when the cage body is rotated 90° after the cage is inserted in between the pair of upper and lower vertebral bodies, a large number of projections formed on both upper and lower surfaces are opposed to the upper and lower vertebral bodies, and the large number of projections bite into the vertebral bodies. Therefore, after the cage is placed between the vertebral bodies, the cage is not displaced in position, and the cage can be placed stably between the vertebral bodies.

Further, because tip end surfaces of the large number of upper and lower projections match the arc curved surface, concave curved surfaces of the upper and lower surfaces in the upper and lower vertebral bodies can be dealt with.

BRIEF DESCRIPTION OF THE ACCOMPANYING DRAWINGS

The above and further objects and novel features of the present invention will more fully appear from the following detailed description when the same is read in conjunction with the accompanying drawings, in which.

DETAILED DESCRIPTION OF THE PREFERRED EMBODIMENTS

Figure 1:
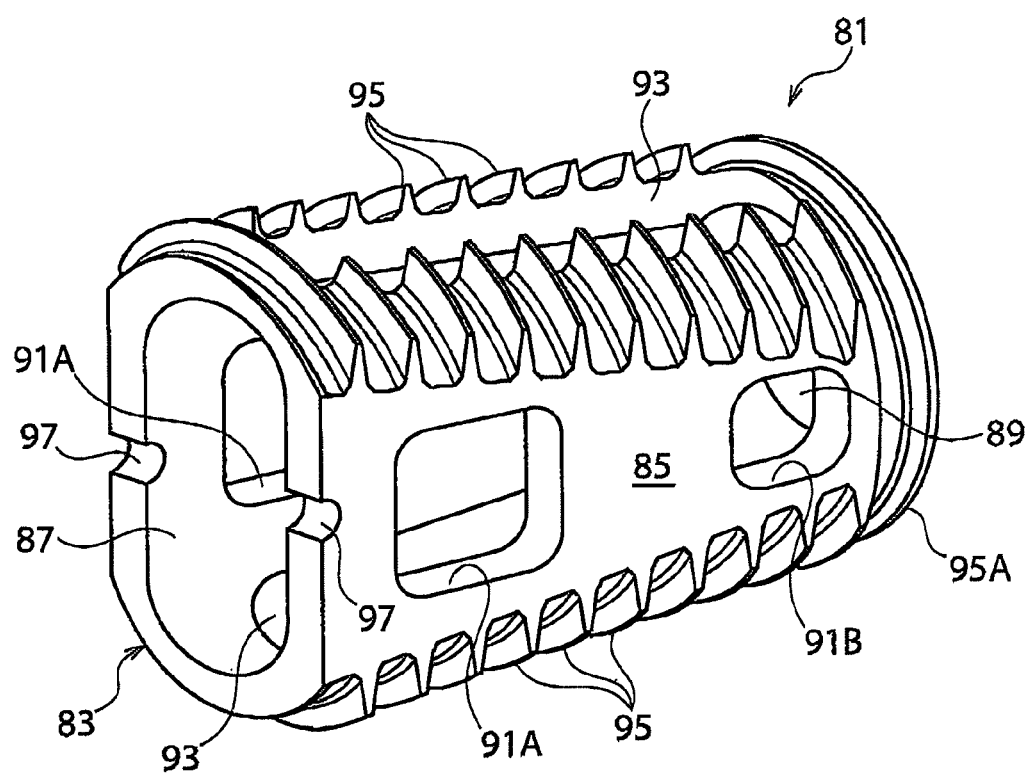
FIG. 1 is an explanatory perspective view showing a structure of a conventional cage.

There will be detailed below the preferred embodiments of the present invention with reference to the accompanying drawings. Like members are designated by like reference characters.

Figure 2:
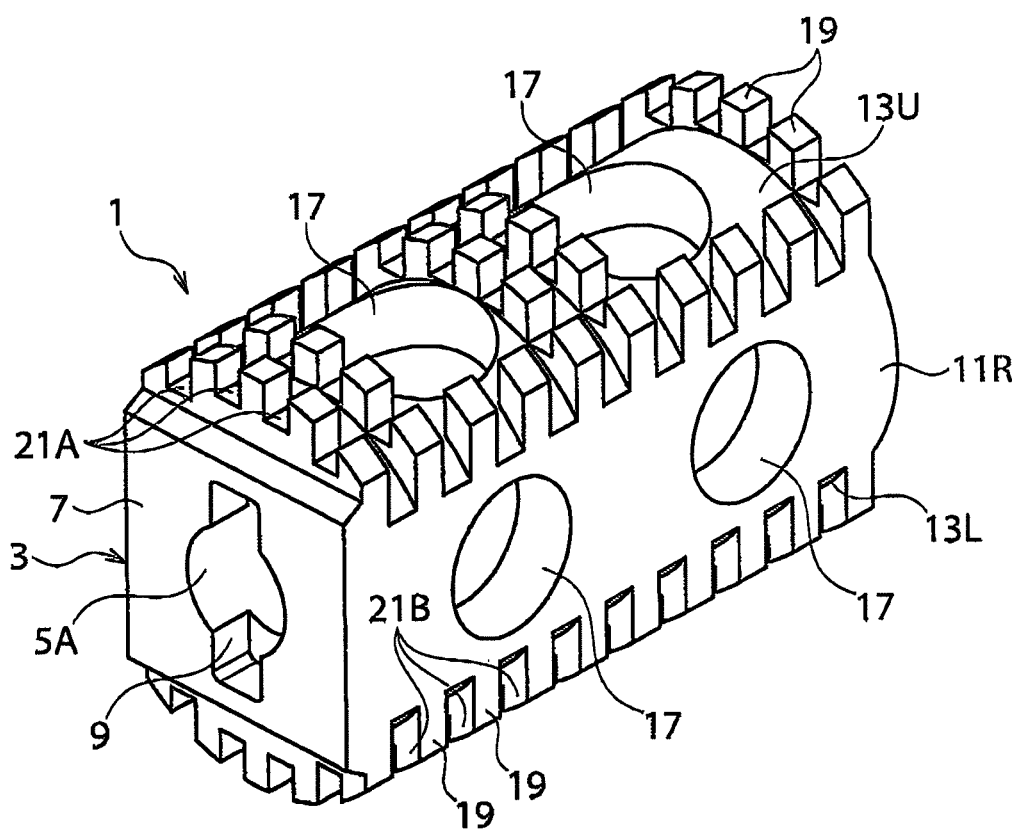
FIG. 2 is an explanatory perspective view of a front side of a cage according to first embodiment of the present invention.
Figure 3:
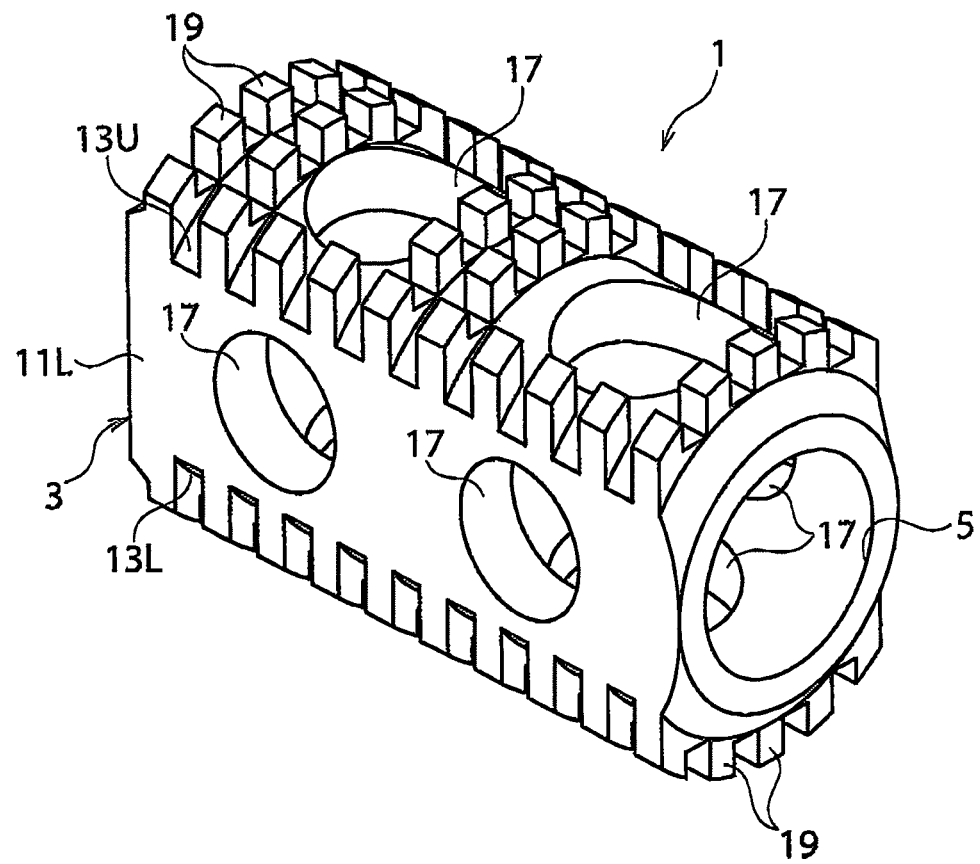
FIG. 3 is an explanatory perspective view of a back side of the cage according to the first embodiment.

With reference to FIG. 2 and FIG. 3, a cage 1 according to a first embodiment of the present invention includes a cage body 3. The cage body 3 is formed long in its longitudinal direction and the cage body 3 is formed with a large-diameter longitudinal through hole 5 penetrating the cage body 3 in its longitudinal direction. A front end (small-diameter hole) 5A of the through hole 5 is formed as a small-diameter hole formed in a front end wall portion 7 of the cage body 3. Tool engaging recesses 9 with which a tool (not shown) is engaged are formed in upper and lower portions of the small-diameter hole 5A.

Left and right side surfaces 11L and 11R of the cage body 3 are flat smooth surfaces which are parallel to each other. Upper and lower surfaces 13U and 13L of the cage body 3 are formed in an arc curved surface, which are arc around an axis 15 (see FIG. 4) of the cage body 3 in the longitudinal direction. That is, the cage body 3 has such a general shape such that both left and right sides of a cylindrical body are cut flatly and side surfaces 11L and 11R are formed. Communication holes 17 with an appropriate number that are in communication with the through hole 5 are provided in the left and right side surfaces 11L and 11R and the upper and lower surfaces 13U and 13L of the cage body 3 on the same plane intersecting with the axis 15 at right angles. These communication holes 17 have the same shapes and sizes. In the first embodiment, the communication holes 17 have a common diameter and are formed into circular holes to avoid stress concentrations.

Further, a large number of projections 19 having small square cross-sectional shapes are provided on both upper and lower surfaces 13U and 13L of the cage body 3 such that the projections 19 are independent in the longitudinal direction and the lateral direction. The projecting lengths of the projections 19 from both the upper and lower surfaces 13U and 13L are substantially equal to each other, and tip end surfaces of the projections 19 substantially match with the arc curved surface formed around the axis 15. A plurality of parallel grooves 21A are formed in both the upper and lower surfaces 13U and 13L of the cage body 3, and a plurality of grooves (peripheral grooves) 21B in the lateral direction are formed in the upper and lower surfaces 13U and 13L of the cage body 3 in the longitudinal direction, and the projections 19 are regions sectioned by these grooves 21A and 21B.

In other words, the large number of projections 19 are formed by providing the longitudinal grooves 21A in parallel in the circumferential direction in the arc curved surface of the cage body 3, and by providing the circumferential grooves 21B in parallel in the longitudinal direction in the arc curved surface of the cage body 3. Thus, the large number of projections 19 can be easily formed.

The width size of the cage body 3 in the lateral direction is smaller than the width size thereof in the vertical direction. That is, the widthwise size between the left and right side surfaces 11L and 11R is smaller than a diameter of the arc curved surface with which the tip ends of the projections 19 on both the upper and lower surfaces.

The large number of projections 19 can be also formed by providing a thread on both upper and lower surfaces of the cage body 3, and by dividing the thread into a plurality of threads by the longitudinal grooves 21A. Further, the grooves 21A and 21B can be formed such that they intersect with each other at right angles as described above, or can be formed such that the grooves 21A and 2113 intersect with each other diagonally like cross hatching. The projections 19 can be also formed into a pin-like shape.

In the structure described above, as shown in FIG. 4, to place the cage 1 between the pair of upper and lower vertebral bodies (vertebrae) 23 after a degenerative intervertebral disk is removed, the cage 1 is made to topple such that the left and right side surfaces 11L and 11R of the cage 1 are opposed to the upper and lower vertebral bodies 23, i.e., such that the side surfaces 11L and 11R become upper and lower surfaces. The cage 1 is inserted between the upper and lower vertebral bodies 23 in a state that the cage 1 is toppled.

As described above, when the cage 1 is inserted between the upper and lower vertebral bodies 23, because the side surfaces 11L and 11R opposed to the upper and lower vertebral bodies 23 are a smooth surface, the resistance generated when the cage 1 is inserted is small and the cage can be easily inserted. After the cage 1 is inserted between the upper and lower vertebral bodies 23 and the cage 1 is positioned, if the cage 1 is rotated rightward or leftward 90° by a tool, the upper and lower surfaces 13U and 13L having the large number of projections 19 are opposed to the upper and lower vertebral bodies 23.

In this case, the tip ends of the large number of projections 19 substantially match with the arc curved surface formed around the axis 15 of the cage 1 in its longitudinal direction. Therefore, because both the upper and lower surfaces of the vertebral bodies 23 are concave curved surfaces, even when the tip ends of the projections 19 interfere with the upper and lower vertebral bodies 23, the cage 1 can be easily rotated. Because both of the upper and lower surfaces of the cage 1 are opposed to the upper and lower vertebral bodies 23, stress is concentrated on the tip ends of the large number of projections 19, the tip ends of the projections 19 bite into the upper and lower vertebral bodies 23, and the cage 1 does not move from the home position where the cage 1 is positioned. Therefore, the cage 1 can be easily inserted between the upper and lower vertebral bodies 23, and it is possible to prevent the cage 1 from moving from the home position.

Figure 4:
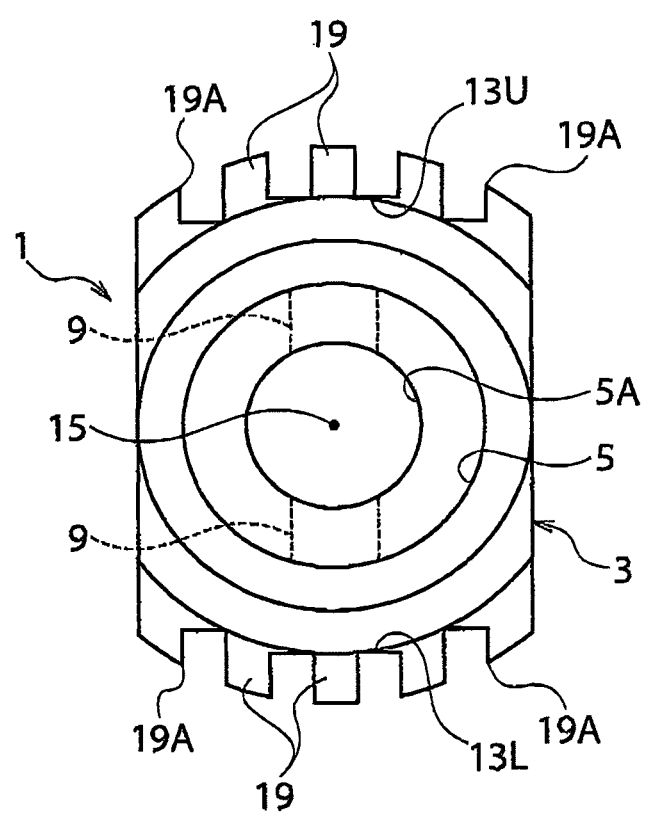
FIG. 4 is an explanatory rear view of the cage according to the first embodiment.

As is apparent from FIG. 4, because the tip ends of the large number of projections 19 match with the arc curved surface, angles of end edges 19A on the inner side of the projections 19 close to the left and right side surfaces become more acute, and the biting properties into the upper and lower vertebral bodies 23 are further enhanced. That is, it is possible to effectively prevent the positional displacement.

Figure 5:
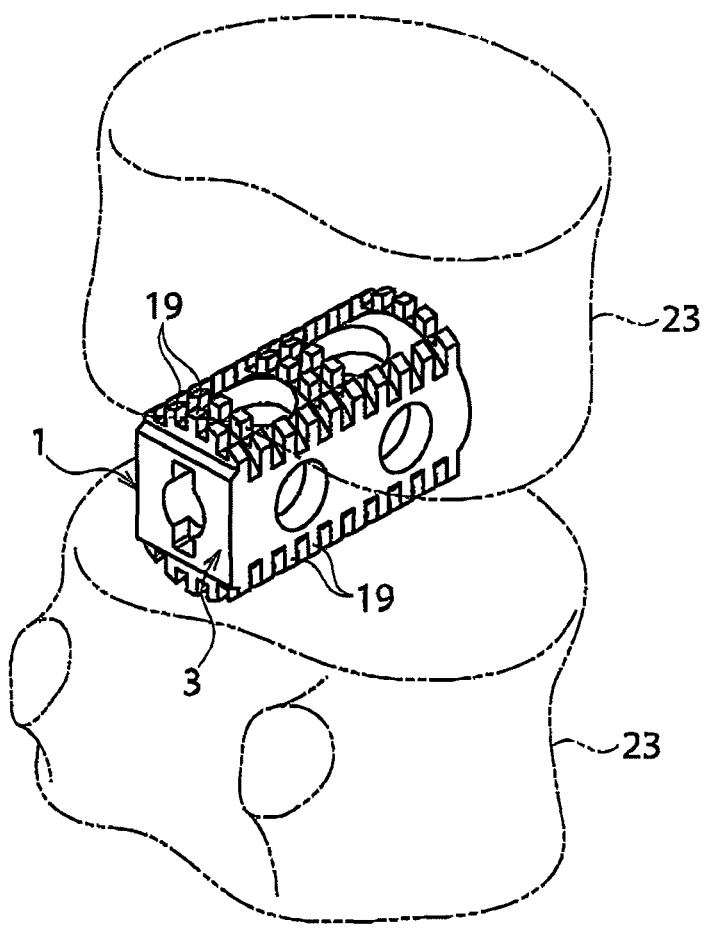
FIG. 5 is an explanatory diagram showing a state that the cage is placed between upper and lower vertebral bodies.
Figure 8:
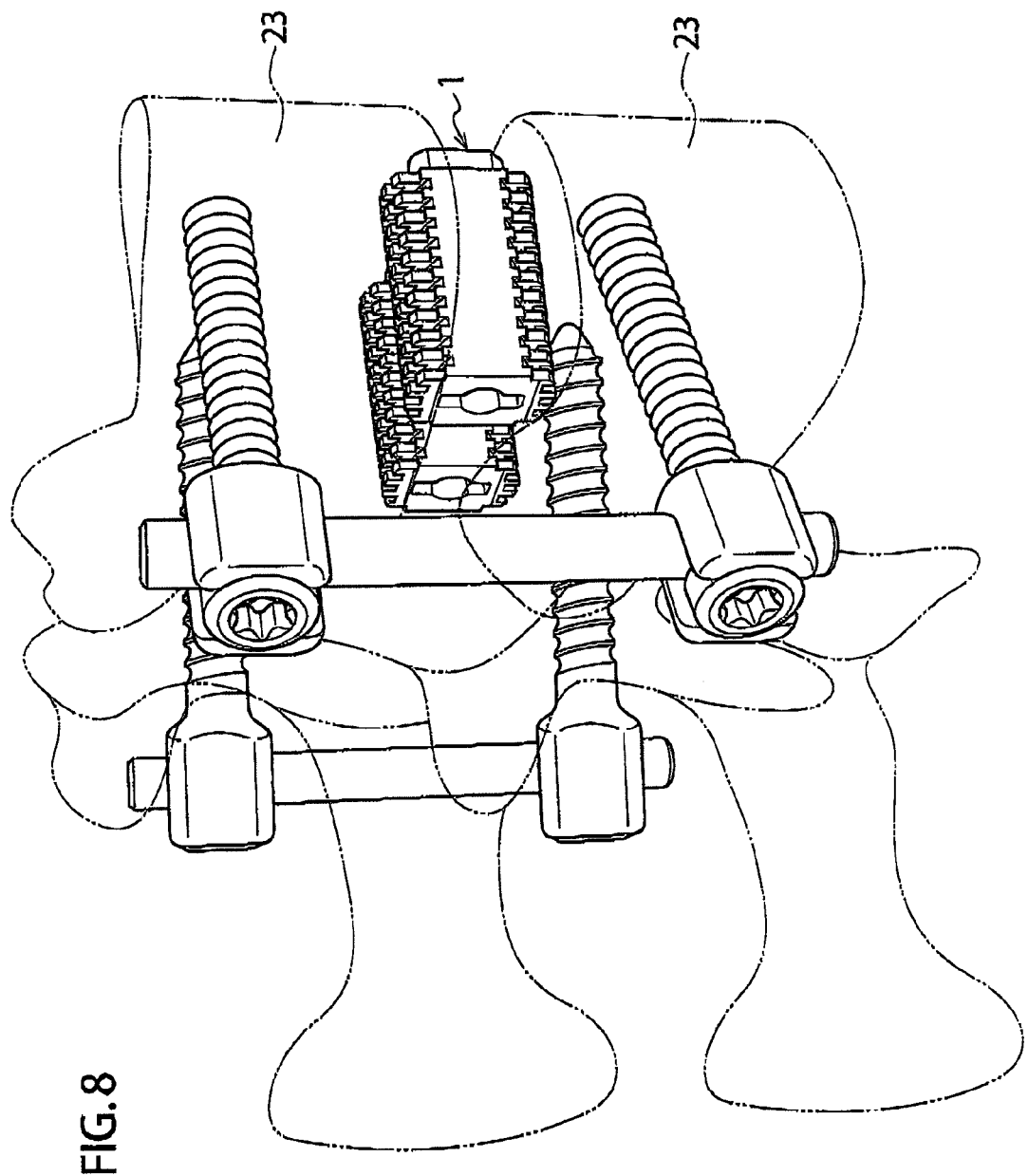
FIG. 8 is an explanatory diagram showing an actual usage example of the cage.
Figure 9:
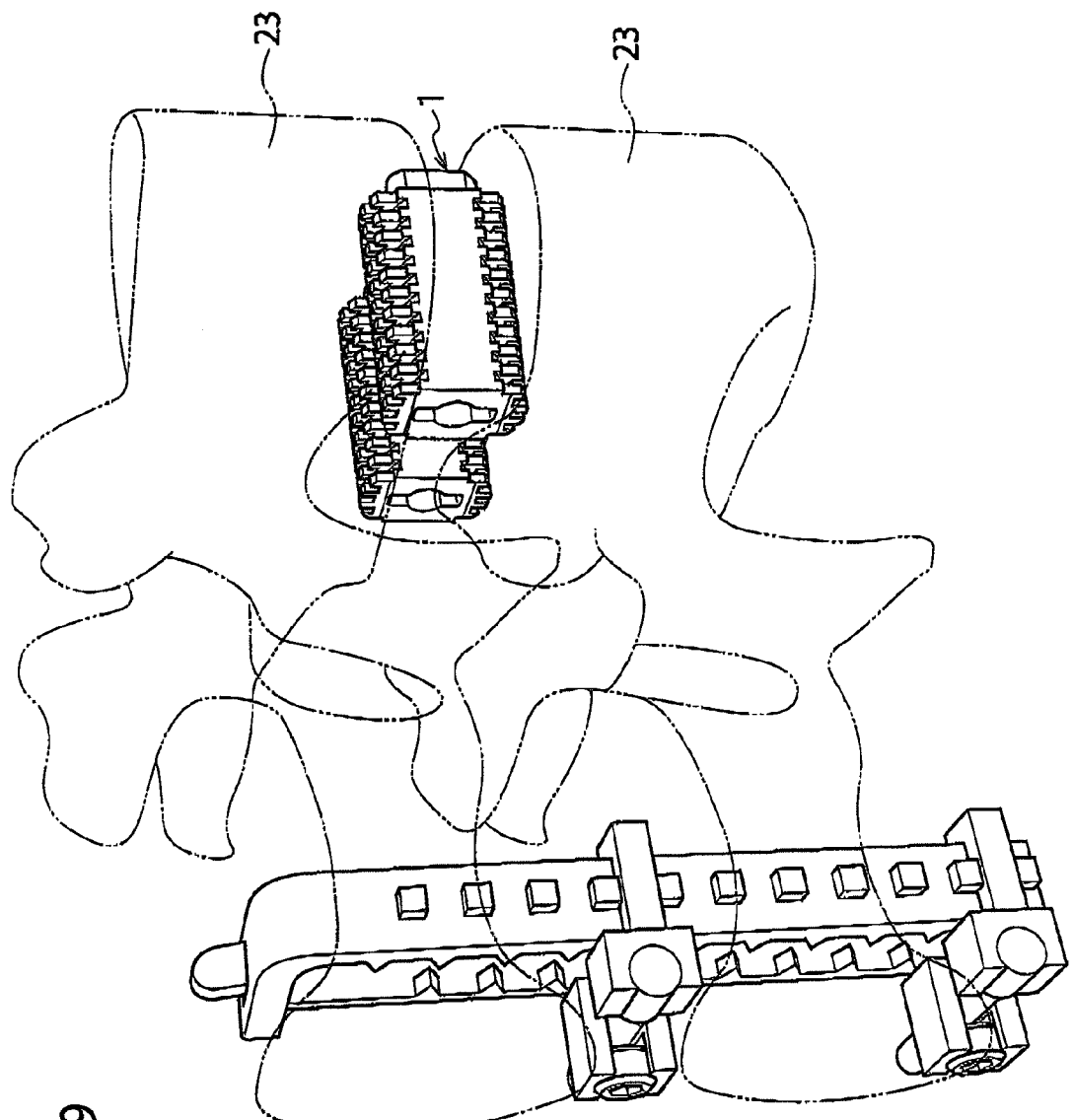
FIG. 9 is an explanatory diagram showing an actual usage example of the cage.

While FIG. 5 shows that one cage 1 is placed between the upper and lower vertebral bodies 23, two cages 1 are placed side by side between the upper and lower vertebral bodies 23 as shown in FIG. 8 and FIG. 9.

As is understood from the above descriptions, because both the upper and lower surfaces of the cage body 3 are provided with the large number of projections 19, the biting properties with respect to the upper and lower vertebral bodies 23 are enhanced, and the stability of the cage placed between the upper and lower vertebral bodies 23 is enhanced.

Further, because the cage body 3 is formed with the large-diameter through hole 5 in the longitudinal direction, a transplanted bone can be accommodated in the through hole 5. The transplanted bone grows through both the left and right side surfaces 11L and 11R and the communication holes 17 formed in the upper and lower surfaces, the transplanted bone can coapt together with the upper and lower vertebral bodies. That is, the coaptation can be facilitated.

Because the left and right side surfaces 11L and 11R of the cage 1 and the communication holes 17 formed in both the upper and lower curved surfaces are formed into the circular holes having a common diameter, stress concentrations can be avoided, the rigidity can be enhanced, and the weight can be reduced. In addition, the communication holes 17 can be easily worked (formed) and the cage 1 can be produced inexpensively.

Figure 6A:
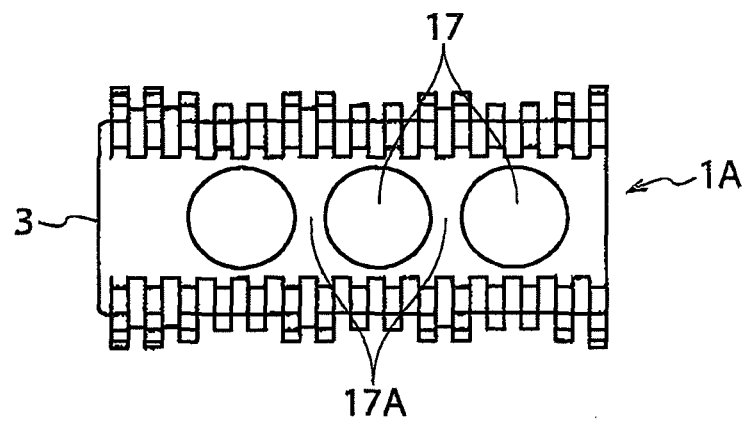
FIGS. 6A and 6B are explanatory diagrams showing a shape of a cage according to a second embodiment of the present invention.
Figure 6B:
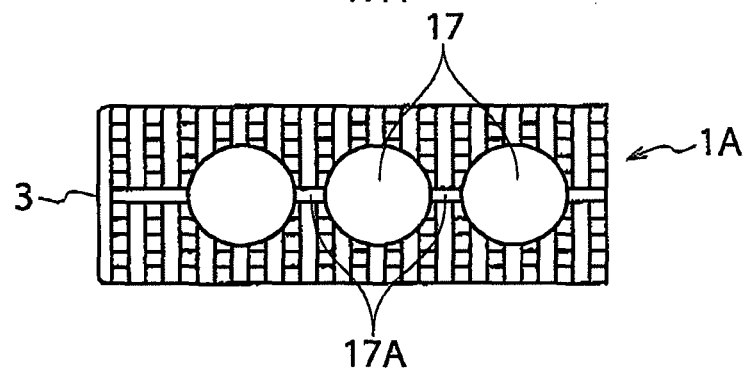

FIGS. 6A and 6B show a cage 1A according to a second embodiment of the present invention. In the cage 1A, a distance 17A between outer peripheral edges of adjacent communication holes 17 formed in the cage body 3 is set smaller than a radius of the communication hole 17. According to this structure, an area where a transplanted bone accommodated in the through hole 5 and a transplanted bone placed outside the cage 1A are in contact with each other is increased, and the coaptation can be effectively facilitated.

Figure 7A:
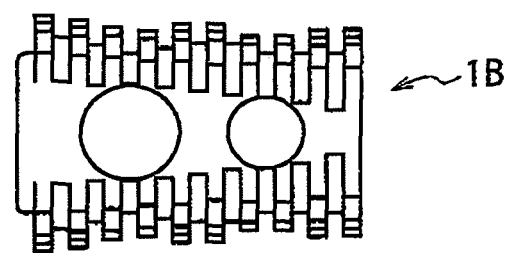
FIGS. 7A and 7B are explanatory diagrams showing a shape of a cage according to a third embodiment of the present invention.
Figure 7B:
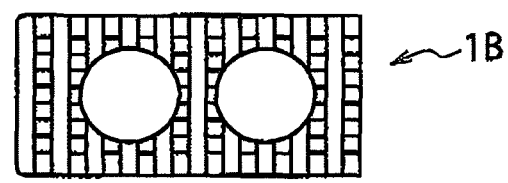

FIGS. 7A and 7B show a cage 1B according to a third embodiment of the present invention. A tip end of the cage 1B is formed in a small-diameter tapered shape, and other structures thereof are the same as those of the cage described above. According to the structure of the third embodiment, because the cage is tapered, the cage can be easily placed between the vertebral bodies, and the same effects as those of the cage described above can be exhibited.

FIG. 8 and FIG. 9 show actual usage examples in which two cages 1 are placed between upper and lower vertebral bodies 23, and the upper and lower vertebral bodies 23 are connected to each other through an appropriate implant such as a screw and a rod.

The entire contents of a Japanese Patent Application P2009-004482 (filed on Jan. 13, 2009) and a Japanese Patent Application P2008-028127 (filed on Feb. 7, 2008) are incorporated herein by reference.

Although the invention has been described above by reference to certain embodiments of the invention, the invention is not limited to the embodiments described above. Modifications and variations of the embodiments descried above will occur to those skilled in the art, in light of the above teachings. The scope of the invention is defined with reference to the following claims.

What is claimed is:

1. A cage configured to be interposed between a pair of vertebral bodies, comprising:
   a cage body;
   a left side surface and a right side surface formed in a left side and a right side of the cage body in a flat, smooth surface manner and parallel to each other;
   an upper surface and a lower surface formed in an upper side and a lower side of the cage body; and
   a plurality of projections arranged in a longitudinal direction and a lateral direction on the upper and lower surfaces of the cage body so as to protrude from the upper and lower surfaces of the cage body, wherein each of the plurality of projections protrude from the cage body in a direction perpendicular to the longitudinal direction and the lateral direction;
   wherein the plurality of projections include tip end surfaces that are arranged in the lateral direction to match with an arc curved surface formed around an axis in the longitudinal direction of the cage body, thereby forming a non-threaded leading edge and permitting insertion of the cage in between the vertebral bodies followed by rotation to a fixed position,
   wherein angles of inner end edges of the projections proximate to the left and the right side surfaces of the cage body along the arc curved surface are more acute than angles of inner edges of the projections positioned in between the projections proximate to the left and the right side surfaces, and
   wherein the projections have square cross-sectional shapes such that the projections are independent in the longitudinal and lateral directions.

2. The cage according to claim 1, wherein a longitudinal through hole is formed in the cage body in its longitudinal direction so as to penetrate the cage body; and
   wherein both of the left and right side surfaces and both of the upper and lower surfaces of the cage body are provided with communication holes which are in communication with the longitudinal through hole.

3. The cage according to claim 2, wherein the communication holes are circular holes having a common diameter; and
   wherein the communication holes formed in both of the left and right side surfaces are located on a first plane intersecting with the axis in the longitudinal direction of the cage body at right angles, and the communication holes formed in both of the upper and lower surfaces are located on a second plane intersecting with the axis in the longitudinal direction of the cage body at right angles.

4. The cage according to claim 3, wherein a distance between outer peripheral edges of the adjacent communication holes formed in both the left and right side surfaces and both the upper and lower surfaces of the cage body is smaller than a radius of the communication hole.

5. The cage according to claim 4, wherein the cage body is tapered in the longitudinal direction of the cage body such that a first tip end of the cage body has a diameter smaller than a second tip end of the cage body.

6. The cage according to claim 1, wherein the upper surface and lower surface of the cage body each include a plurality of parallel grooves provided in the longitudinal direction of the cage body and a plurality of peripheral grooves provided in the lateral direction of the cage body to form the plurality of projections.

* * * * *